US009353332B2

(12) United States Patent
Lewis et al.

(10) Patent No.: US 9,353,332 B2
(45) Date of Patent: May 31, 2016

(54) OIL EXTRACTION AIDS IN GRAIN PROCESSING

(71) Applicant: Solenis Technologies, L.P., Schaffhausen (CH)

(72) Inventors: Scott R Lewis, Wilmington, DE (US); Paul W. Shepperd, III, Newark, DE (US)

(73) Assignee: Solenis Technologies, L.P., Wilmington, DE (US)

( * ) Notice: Subject to any disclaimer, the term of this patent is extended or adjusted under 35 U.S.C. 154(b) by 0 days.

(21) Appl. No.: 14/121,391

(22) Filed: Aug. 29, 2014

(65) Prior Publication Data

US 2015/0184112 A1 Jul. 2, 2015

Related U.S. Application Data

(60) Provisional application No. 61/870,946, filed on Aug. 28, 2013.

(51) Int. Cl.
*C11B 13/00* (2006.01)
*C11B 1/10* (2006.01)
*C12P 7/06* (2006.01)

(52) U.S. Cl.
CPC . *C11B 13/00* (2013.01); *C11B 1/10* (2013.01); *C12P 7/06* (2013.01); *Y02W 30/74* (2015.05)

(58) Field of Classification Search
None
See application file for complete search history.

(56) References Cited

U.S. PATENT DOCUMENTS

| 5,053,231 | A | 10/1991 | Riffkin et al. |
| 7,497,955 | B2 | 3/2009 | Scheimann et al. |
| 7,602,858 | B2 | 10/2009 | Dally |
| 7,608,729 | B2 | 10/2009 | Winsness et al. |
| 8,841,469 | B2 | 9/2014 | Shepperd et al. |
| 8,962,059 | B1 | 2/2015 | Froderman et al. |
| 2004/0087808 | A1 | 5/2004 | Prevost et al. |
| 2006/0006116 | A1 | 1/2006 | Scheimann et al. |
| 2007/0200007 | A1 | 8/2007 | Stevens et al. |
| 2008/0176298 | A1 | 7/2008 | Randhava et al. |
| 2010/0331580 | A1 | 12/2010 | Ridgley |
| 2011/0283602 | A1 | 11/2011 | Gallop et al. |
| 2012/0245370 | A1 | 9/2012 | Sheppard et al. |
| 2013/0109598 | A1 | 5/2013 | Nacson |
| 2014/0275589 | A1 | 9/2014 | Blankenburg et al. |
| 2015/0009485 | A1 | 1/2015 | Mheen et al. |

OTHER PUBLICATIONS

Majoni et al., Physical and Chemical Processes to Enhance Oil Recovery from Condensed corn Distillers solubles, J Am Oil Chem Soc, vol. 88, pp. 425-434 (2011).
Taherzadeh et al., "Enzyme-based hydrolysis process for ethanol from ignocellulosic materials: a review", Bio Resources, vol. 2, No. 4, 2007, pp. 707-738.
Davis, "Corn Milling, Processing and Genration of Co-Products", Minnesota Nutrition Conference, Technical Symposium, 11, 2001.
Klinkesorn et al., "Stability and Rheology of Corn Oil-in-Water Emulsions Containing Maltodextrin", Food Research International, vol. 37, pp. 851-859, 2004.

(Continued)

*Primary Examiner* — Yate K Cutliff
(74) *Attorney, Agent, or Firm* — Joanne Rossi; Michael J. Herman

(57) ABSTRACT

A method is provided for the use of a process additive system to improve the separation of oil from a process stream (whole stillage, thin stillage, or syrup) generated as a byproduct in grain to ethanol production.

20 Claims, 1 Drawing Sheet

(56) References Cited

OTHER PUBLICATIONS

Wang, et al., "Effect of Low-Shear Extrusion on Corn Fermentation and Oil Partition", J. Agricultural and Food Chemistry, vol. 57, pp. 2302-2307, 2009.
Kadioglu et al., "Surfactant-Based Oil Extration of Corn Germ", J AM Oil Chem Soc, vol. 88, pp. 863-869, 2011.
The Merck Index, "Polysorbates", 12th Ed. Entry #7742, p. 1308, 1996.
Tadros, T., Surfactants, Kirk-Othmer Encyclopedia of Chemical Technology, 2006.
Jacques, KA et al., The Alcohol Textbook, 4th Ed., p. 401, 2003.
International Search Report, PCT/US2014/000186, p. 1, Nov. 13, 2014.

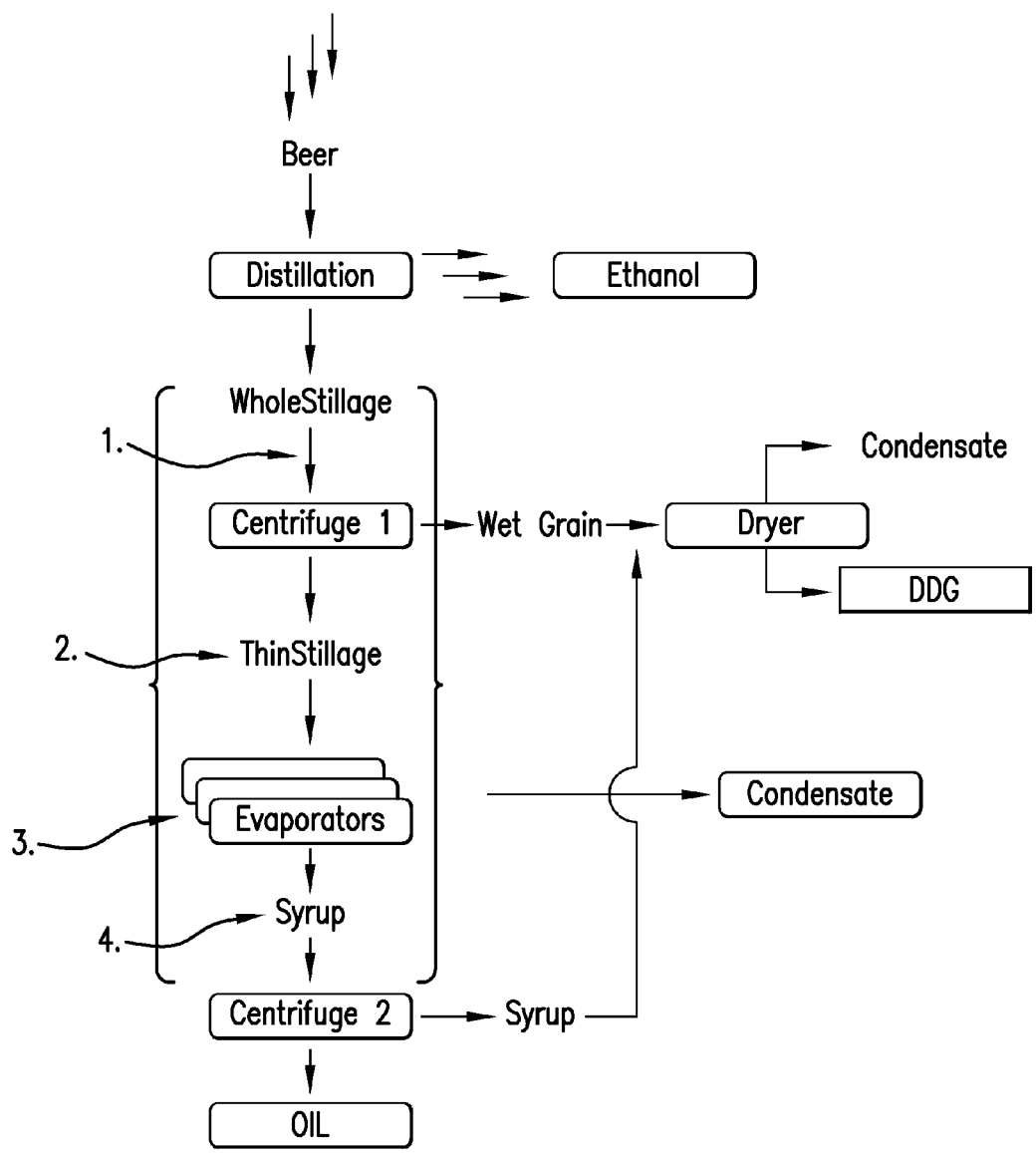

OIL EXTRACTION AIDS IN GRAIN PROCESSING

This application claims the benefit of U.S. provisional application No. 61/870,946 filed on Aug. 28, 2013, the entire contents of which are herein incorporated by reference.

FIELD OF THE INVENTION

This invention pertains to recovering oil in grain to ethanol production.

BACKGROUND OF THE INVENTION

There are two types of grain to ethanol processing, wet milling and dry milling. The central difference between the two processes is how they initially treat the grain. In wet milling, the grain is steeped in water, and then separated for processing in the first step. Dry milling, which is more common, requires a different process.

The corn dry milling process, also referred to as the dry grind process in this document, utilized in the production of ethanol is well known. For example see Kelly S. Davis, "Corn Milling, Processing and Generation of Co-Products", Minnesota Nutrition Conference, Technical Symposium, 11 Sep. 2001. Ethanol plants typically treat whole stillage from the beer column via centrifugation to produce wet cake and thin stillage then further treat the thin stillage stream by subjecting it to multiple effect evaporation to produce increase the solids and recover the distillate for return use in the process (FIG. 1). As solids increase the thin stillage is typically referred to as syrup (see FIG. 1). The syrup may be sold as a product, but is more typically combined with wet cake or distillers dry grains and sold as animal feed. These processes are well known in the industry and are generally employed in plant design in the industry.

In an effort to take advantage of co-product streams, many plants have added oil removal processes in which the thin stillage or syrup is subjected to processes, such as centrifugation or extraction, to remove corn oil from the syrup. This corn oil is also known as distillers corn oil (DCO). For example, the application of centrifuges to the separation of corn oil from syrup is in wide use in the fuel ethanol industry. While the theoretical yield of oil per bushel of processed corn is 1.6 pound per bushel, many of the commercial installations fall far short of this. Increasing the corn oil production of a plant by 0.1 gallons per minute equates to an additional 400,000 pounds per year of additional oil production. This represents a significant source of additional revenue for the plant.

Recently there has been effort directed at increasing the value model of the corn to ethanol production process by extracting the oil from the thin stillage byproduct. U.S. Pat. No. 7,602,858 B2 describes a mechanical method of separating the oil from concentrated thin stillage, referred to as the "syrup", using a disk stack centrifuge. U.S. Pat. Appl. No. 2008/0176298 A1 teaches the use of an alkyl acetate solvent for extraction of corn oil in an ethanol production process.

Of particular interest are technologies which do not require the adoption of capital expenditures to implement a new mechanical solution and/or significant process change such as the use of an extraction solvent that requires recycling. U.S. Pat. Appl. No. 2012/0245370 A1 describes a method to improve the oil extraction process. When using known methods there is still some oil that is not recovered from the syrup. There is opportunity to further improve the oil recovery process.

Also of particular interest are technologies which employ process additives which have long shelf stability and are easily pumped and handled.

SUMMARY OF THE INVENTION

The present invention discloses a method for improving the separation of oil from process streams (whole stillage, and/or thin stillage, and/or syrup) generated as a byproduct in grain, such as corn or wheat, to ethanol production. The method consists of adding a process additive system comprising at least one chemical additive and at least one hydrophobic silica to a grain, such as corn or wheat, to ethanol process stream. The method involves treating any of the process streams down stream of the distillation operation in grain to ethanol production with a process additive system which enhances the mechanical separation of oil from said streams.

Preferably the process additive system comprises materials that are recognized as safe such that it does not compromise the potential end use of the resulting distillers dried grains with solubles (DDGS) or wet distillers grains with solubles (WDGS) as a feedstock.

In some instances the invention can provide the benefit of 1) increasing oil productions above that obtained with prior methods; and/or 2) producing cleaner oil (high quality) by minimizing the suspended solids and/or water content of the resultant oil; and/or 3) reducing the maintenance of the centrifuge in the manner of reduced deposited materials thereby lessening the need for outages and cleanings as well as permitting extension of time between backflush purges leading to increased production and less down time also providing the value of simpler and easier cleaning of the centrifuge at outages; and/or 4) reducing maintenance of the evaporators in the manner of reduced deposited materials decreasing the frequency and complexity of cleanings, decreasing down time, and reducing costs.

BRIEF DESCRIPTION OF THE FIGURES

FIG. 1: Partial generic overview representative of corn to ethanol production indicating some addition points for the chemical additive: point 1—to the whole stillage prior to separation into wet cake and thin stillage, at or near the inlet to centrifuge 1; point 2—at or near the inlet of the evaporator; point 3—directly into the evaporator(s); point 4—to a point prior to or at the inlet of the oil centrifuge, centrifuge 2.

DETAILED DESCRIPTION OF THE INVENTION

The present invention discloses a method for improving the separation of oil from process streams (whole stillage and/or, thin stillage and/or syrup) generated as a byproduct in grain to ethanol production. Corn is the most common grain used but other grains such as wheat, sorghum (milo), and barley can also be used. The method consists of adding a process additive system comprising at least one chemical additive and at least one hydrophobic silica to a grain, preferably corn, to ethanol process stream. The method involves treating any of the process streams downstream of the distillation operation in grain, preferably corn, to ethanol production with a process additive system which enhances the mechanical separation of oil from said streams.

The present invention discloses a method for improving the separation of oil from the whole stillage, the thin stillage or the syrup processing operation in grain, preferably corn, to ethanol production, preferably employing a dry milling process, to provide for an increase in oil yield.

The present invention describes a method for recovering oil from grain, preferably corn, to ethanol production, the method consists of the addition of a process additive system comprising at least one chemical additive and at least one hydrophobic silica with a particle size of greater than 0.01 μm or greater than 0.1 μm, or greater than 0.5 μm, or greater than 1 μm present and the silica in an amount of from 3% to 50% by weight based on the total weight of the process additive system. The chemical additive is in an amount of at least 20% of the process additive system, and can comprise up to 97% of the process additive system. Modifiers that may prove beneficial are those added to modify the sedimentation stability, rheological properties such as viscosity and thixotropy, and/or elastic properties of the process additive system.

In one aspect of the invention, the method comprises application of the process additive system to the thin stillage process stream and/or syrup concentrate prior to the oil separation step. Preferably the oil separation from the concentrated syrup is achieved by a mechanical operation such as a membrane or centrifuge. The separation can be achieved by a centrifuge such as a disk stack or horizontal tricanter centrifuge. Other mechanical separators can also be used in the present invention including, but not limited to, reverse centrifugal cleaners.

In another aspect of the invention, the method comprises application of the process additive system to the whole stillage prior to separation into thin stillage and wet cake.

In another embodiment, the process additive system may be added to the grain to ethanol process streams via more than one addition point. The process additive systems added at each point does not need to have the same composition or be added at the same dosage as long as the total amounts of each component and the total dosage of all the addition point combined fall within the range specified for the process additive system.

FIG. 1 is a partial generic overview representative of corn to ethanol production. In a typical corn to ethanol process, after a number of different mashing and fermentation steps, the corn is converted to material referred to as "beer". The beer is then processed through a distillation process to separate the crude ethanol, leaving a stillage byproduct known as whole stillage. The whole stillage is subjected to a solid separation centrifugation process to yield distillers wet grain and thin stillage. The thin stillage is then typically processed through a number of evaporator units to yield the concentrated syrup. This syrup may then be further processed, for example by oil separation centrifugation, to separate the oil from the syrup. The remaining syrup is then typically combined with the distillers wet grain and dried, to yield distillers dried grains with solubles (DDGS). The process additive system of the present invention is typically added to the process stream at different points in the separation process. Some preferred addition points are shown in FIG. 1. The areas in the process where the process additive system is typically charged are designated by the bracketed ("{ . . . }") area in the diagram.

The process additive system may be added at different points in the separation system. Addition points for the process additive system include, but are not limited to, the whole stillage process stream prior to separation into wet cake and thin stillage, the process stream at or near the inlet to the centrifuge or after the solid separation centrifuge. The process additive system can be added, prior to or at the inlet and/or outlet of one or more of the thin stillage evaporators, in the evaporators, to the syrup just prior to the oil separation centrifuge and/or at the inlet of the premix or retention heat tanks, and a point after the syrup feed tank and before the centrifuge.

Process additive systems useful in the present invention are those which provide an increase in oil production. The application of the process additive systems could comprise of one or more addition points within the thin stillage processing unit operation. The process additive systems can be applied to the syrup resulting from concentration of the thin stillage in an evaporator. Process additive systems useful in the present invention comprise at least two components; a chemical additive and a hydrophobic silica and optionally modifiers.

Chemical additives are one component of the process additive system. Such additives useful in the present invention are functionalized polyols derived from a sorbitol, a sorbitan, isosorbide, sucrose, or glycerol, including 1,4-sorbitan. Preferred chemical additives are functionalized polyols comprising alkoxylated sorbitan monoalkylates, alkoxylated sorbitan dialkylates, alkyoxylated sorbitan trialkylates and mixtures thereof. The alkoxylated alkylates of sorbitan have an alkyl chain length of from about 6 to about 24 carbons, or from about 8 to about 18 carbons, preferable the alkoxylated sorbitan alkylates are alkoxylated esters of sorbitan. The alkoxylated alkyate of sorbitan is preferably alkoxylated with from about 5 to about 100 moles of alkyl oxide, or from 5 to 60 moles, or from about 10 to about 30 moles, or from about 12 to about 30, or from about 12 moles to about 25 moles. Preferable the alkoxylated sorbitan alkylates are alkoxylated esters of sorbitan. The preferred alkyl oxides are ethylene oxide and propylene oxide or a combination thereof. Preferred alkoxylated alkylate of sorbitan are sorbitan monolaurate, sorbitan monooleate, sorbitan monopalmitate or sorbitan monostearate that have been alkoxylated with less than 50 moles or less than 30 moles of ethylene oxide or propylene oxide or a combination thereof. More preferred alkoxylated alkylates of sorbitan are sorbitan monolaurate, sorbitan monooleate, sorbitan monopalmitate or sorbitan monostearate that have been ethoxylated with from about 10 moles to about 30 moles of ethylene oxide or propylene oxide or a combination thereof, preferably the alkoxylated sorbitan alkylates are alkoxylated esters of sorbitan. More preferred alkoxylated alkylates of sorbitan are sorbitan monolaurate, sorbitan monooleate, sorbitan monopalmitate or sorbitan monostearate that have been alkoxylated with from about 12 moles to about 25 moles of ethylene oxide or propylene oxide or a combination thereof, preferably the alkoxylated sorbitan alkylates are alkoxylated esters of sorbitan. Compositions/grades of this class of materials that are, or could be, classified as recognized as safe such that they do not comprise the potential end use of the resulting dry distiller grain as a feedstock are preferable for the invention.

Additional classes of chemical additives that may be useful in the present application are alkoxylated esters of sorbitan, alkoxylated fatty alcohols, alkoxylated fatty acids, sulfonated alkoxylates, alkyl quaternary ammonium compounds, alkyl amine compounds, alkyl phenol ethoxylates and mixtures thereof. Additional classes of additives that may be useful for the invention include fatty acid salts (sodium, ammonium or potassium) and low molecular weight silicone surfactants. The alkoxylate portion of the forgoing classes of chemicals may be any mixture of ethylene oxide and propylene oxide added in block or random fashion to the base molecule. The most preferred are the alkoxylated esters of sorbitan alkoxylated with from about 5 to about 100 moles of alkyl oxide, or from 5 to 60 moles, or from about 10 to about 30 moles, or from about 12 to about 30, or from about 12 moles to about 25 moles.

Silicas are the second component of the process additive system. Useful silicas in the present invention are hydrophobized silicas produced from precipitated silicas, fumed silicas, colloidal silicas, thermal silicas, or silica gels. These synthetic silicas are amorphous. Preferred hydrophobic silicas comprise hydrophobic precipitated silicas, hydrophobic fumed silicas, and mixtures thereof. Examples of commercially available precipitated hydrophobic silicas include the Sipernat® D-series (Evonik Corporation, Parsippany, N.J.), Perform-O-Sil (Performance Process, Inc., Mundelein, Ill.), and Dumacil (Hi-Mar Specialty Chemicals, LLC, Milwaukee, Wis.) product lines. Examples of commercially available fumed hydrophobic silicas include the Aerosil® R-series (Evonik Corporation, Parsippany, N.J.), Profusil (Performance Process, Inc., Mundelein, Ill.), Cab-O-Sil® TS-series (Cabot Corporation, Billerica, Mass.), and HDK® H-series (Wacker Chemical Corporation, Adrian, Mich.) product lines.

The particle size of the silicas referenced in this invention indicates the median particle diameter ($d_{50}$) as determined by laser diffraction.

It is well-known to those skilled in the art that hydrophobized silicas as produced often exist as agglomerates comprised of aggregates and primary subunits. Aggregates are defined as joined primary subunits whose surfaces are attached to each other, which usually cannot be separated by a dispersion process. Agglomerates are defined as loose clusters of primary subunits and/or aggregates that can be separated by dispersion (DIN 53206). Due to the nature of the manufacturing process of synthetic silicas, there exists a distribution of particle sizes for a given silica product. A given hydrophobic silica product may consist of a mixture of agglomerates, non-agglomerated aggregates, and/or non-aggregated primary subunits. Particle size measurements, as referenced above, measure the largest form in which the silica is present. For example, if three aggregates are unagglomerated, particle size measurements will indicate the presence of three particles corresponding to the size of each of the aggregates. However, if the three aggregates are present as one agglomerated particle, the particle size measurements will indicate the presence of one particle corresponding to the agglomerated particle size. Although the fumed silica particles are generally smaller than precipitated silicas, this is not always the case as they can form agglomerates well in excess of 10 µm. Silicas of increased surface area generally have increased thickening ability. It is well-known to those skilled in the art that the manufacturing processes for producing precipitated and fumed silicas can be adjusted in order to produce silicas of varying particle size, specific surface area, and other properties. It is also well-known to those skilled in the art that various processes can be used to de-agglomerate these agglomerates and/or de-aggregate particle aggregates in order to obtain a desired particle size and/or particle size distribution. One of the main differences between fumed and precipitated silicas is the presence of a higher density of silanol groups on the surface of precipitated silicas.

Various particle sizes of the silica are useful in this invention. Useful hydrophobic silica particle sizes include from about 0.01 µm to about 200 µm, from about 0.01 µm to about 100 µm, from about 0.01 µm to about 60 µm, from about 0.1 µm to about 200 µm, from about 0.1 µm to about 100 µm, from about 0.1 µm to about 60 µm, from about 0.5 µm to about 200 µm, from about 0.5 µm to about 100 µm, from about 0.5 µm to about 60 µm, from about 1 µm to about 200 µm, from about 1 µm to about 100 µm, from about 1 µm to about 60 µm.

The hydrophobic silicas can be a mixture various silicas with different particles sizes. One could mix various sizes to create a process additive system containing particles as small as 0.01 µm and as large as 200 µm, as small as 0.05 µm and as large as 200 µm, as small as 0.1 µm and as large as 100 µm, as small as 0.5 µm and as large as 100 µm. For example a silica with a small particle size can be mixed with a silica of large particle size to obtain a mixture of silica with an overall desired particle size Additionally, it may be desirable to adjust the sedimentation stability, rheological properties such as viscosity and thixotropy, and/or elastic properties of the process additive system. Substances that may be useful for this and other purposes include smaller particle size hydrophobic or hydrophilic silica and/or modifiers such as fatty acid alkyl esters, monoglycerides, diglycerides, triglycerides, mineral oils, and alcohols.

Silica of smaller particle size can provide additional benefits to the process additive system. Generally these smaller particle size silica are from 0.01 to 20 micron in size. Such silicas can help to control the sedimentation stability, rheological properties, and/or elastic properties of the process additive system. Such silica may be fumed, precipitated, colloidal, thermal, or gels, and mixtures thereof. Preferred hydrophobic silicas comprise hydrophobic precipitated silicas, hydrophobic fumed silicas, and mixtures thereof. Particle sizes of silicas useful to control these properties in this invention may be from about 0.01 µm to about 20 µm, from about 0.01 µm to about 10 µm, from about 0.01 µm to about 5 µm, from about 0.05 µm to about 20 µm, from about 0.05 µm to about 10 µm, from about 0.05 µm to about 5 µm. Generally the particles are less than 10 µm, or less than 5 µm or less than 3 µm. Generally the particles are greater than 0.01 µm greater than 0.05 µm. Silicas of this size may provide the benefit of increasing the sedimentation stability of the process additive system and modifying its rheological and/or elastic properties. Hydrophilic silicas may also be used; however, it should be noted that use of such silicas in high concentrations may result in very high viscosities of the process additive system.

One class of modifiers useful in adjusting the sedimentation stability, rheological properties, and/or elastic properties of the process additive system include a wide variety of mono-, di-, and triglycerides (oils and fats) available from plant and animal sources are known in the food, chemical, and other industries. These include, but are not limited to corn, canola, palm, palm kernel, coconut, peanut, soybean, sunflower, and castor oils as well as lard and tallow. In addition, similar mono-, di-, and triglycerides may be produced using synthetic methods. Another class of modifiers useful in adjusting these properties is fatty acid alkyl esters, which are alkyl esters of the aforementioned triglycerides and/or similar fatty acids. Examples include soybean methyl esters, canola methyl esters, and soybean ethyl esters. Additional useful modifiers include mineral oils and alcohols. These modifiers can generally be added to lower the viscosity of the process additive system or improve its compatibility with the media into which it is being added.

In general the amount of chemical additive in the process additive system is from 20 to 97% of the total process additive system, or from 20 to less than 95% of the total process additive system or from 40 to less than 95% of the total process additive system.

In general it is advantageous to have a total silica concentration in the process additive system of from 3% to 50% by weight based on the total process additive system, from 3% to 40% by weight based on the total process additive system, from 3% to 30% by weight based on the total process additive system wherein the silica content includes all silicas added to the process additive system. The total silica concentration may be from greater than 5% up to 50% by weight based on the weight of the total process additive system, from greater than 5% up to 40% by weight, based on the total process additive system from greater than 5% up to 30% by weight based on the total process additive system wherein the silica content includes all silicas added to the process additive system.

If smaller particle size silica is used to adjust the sedimentation stability, rheological properties, and/or elastic properties of the process additive system for the designated end-use, it may be used in an amount of from about 0.1% to about 80% by weight of the total amount of silica in the process additive system, from about 1% to about 80% by weight of the total amount of silica in the process additive system, from about 5% to about 50% by weight of the total amount of silica in the process additive system.

If modifiers such as fatty acid alkyl esters, monoglycerides, diglycerides, triglycerides, mineral oils, and/or alcohols are used to adjust the sedimentation stability, rheological properties, and/or elastic properties of the process additive system for the designated end-use, they may be in an amount of from about 0.1% to about 30% by weight based on the total process additive system, from about 0.1% to about 25% by weight based on the total process additive system, from about 1% to about 25% by weight based on the total process additive system.

The process additive system can be added to the grain, preferably corn, to ethanol process stream (whole stillage, thin stillage or syrup) in an amount of from about 20 to about 10,000 ppm based on the weight of the process stream, from about 20 to about 4000 ppm, from about 20 to about 2000 ppm, from about 20 to about 1500 ppm, from about 50 to about 10,000 ppm based on the weight of the process stream, from about 50 to about 4000 ppm, from about 50 to about 2000 ppm, from about 50 to about 1500 ppm, from about 100 to about 10,000 ppm based on the weight of the process stream, from about 100 to about 4000 ppm, from about 100 to about 2000 ppm, from about 100 to about 1500 ppm.

One embodiment of the invention comprises adding to the grain to ethanol process a composition comprising from 20 to 97% chemical additive, from 3 to 50% hydrophobic silica and optionally 0 to 30% modifiers, wherein the chemical additive is an alkoxylated sorbitan alkylate, added to the grain to ethanol process stream in an amount of from 20 to 10,000 ppm based on the weight of the process stream.

The process additive system can be heated and applied to the process stream (whole stillage, thin stillage or syrup) in a temperature range of from 18° C. to 100° C., from 25° C. to 85° C., from 30° C. to 80° C.

A negative impact of processing the syrup at higher temperatures to improve the yield of oil, for example temperatures greater than 195° F. or 205° F. depending on the process, is that discoloration of the syrup results, which imparts a negative appearance to the DDGS and lessens that value of this material. The higher processing temperatures can cause higher color of the oil itself. As such, an added benefit of the invention is the ability to increase the oil yield at lower processing temperatures and mitigate the potential of the processed syrup to negatively impact the appearance and value of the DDGS and the oil. Reducing processing temperatures also leads to overall energy savings.

EXAMPLES

Raw Materials

The raw materials used in the examples comprise the following. Polysorbate 80, also known as POE (20) sorbitan monooleate. Polysorbate 40, also known as POE (20) sorbitan monopalmitate. Polysorbate 20, also known as POE (20) sorbitan monolaurate. Hydrophobic silica A is a hydrophobized mixture of about 25% by weight precipitated silica with median particle size of 9 μm and 75% by weight precipitated silica with median particle size of about 35 μm. Hydrophobic silica B is precipitated hydrophobic silica with median particle size of 11-13 μm. Hydrophobic silica C is AEROSIL® R 812, a fumed hydrophobic silica with BET surface area of 260±30 $m^2$/g. Both "syrup" and "corn syrup" refer to concentrated thin stillage from dry milling corn to ethanol producers.

Example 1

Polysorbate 80 and blends of Polysorbate 80 with hydrophobic silica A and soybean fatty acid methyl esters were added at a dosage of 537 ppm into the syrup feed line on the inlet side of the pump feeding two disk stack centrifuges in a corn to ethanol process. The resulting corn oil production is shown in Table 1. Oil production increase is compared to baseline data obtained from Polysorbate 80.

TABLE 1

| Component | Composition (wt %) | | |
|---|---|---|---|
| Polysorbate 80 | 100% | 90% | 86% |
| Soybean Fatty Acid Methyl Ester | | 5% | 5% |
| Hydrophobic Silica A | | 5% | 9% |
| Oil Production (gal/min) | 2.96 | 3.07 | 3.15 |
| Oil Production Increase | | 4% | 6% |

As shown in Table 1, the addition of hydrophobic silica to the Polysorbate 80 resulted in an increase in oil production. Increasing the concentration of hydrophobic silica from 5% by weight to 9% by weight resulted in additional oil production.

Example 2

Various Polysorbates were added at a dosage of 537 ppm into the syrup feed line on the inlet side of the pump feeding two disk stack centrifuges in a corn to ethanol process. The resulting corn oil production is shown in Table 2.

TABLE 2

| Component | Oil Production (gal/min) |
|---|---|
| Polysorbate 80 | 2.98 |
| Polysorbate 40 | 3.03 |

As shown in Table 2, Polysorbate 80 and Polysorbate 40 performed similarly.

Example 3

Polysorbate 80 and blends of Polysorbate 80 with hydrophobic silica and fatty acid methyl esters were added at a dosage of 271 ppm into the syrup feed line on the inlet side of the pump feeding two disk stack centrifuges in a corn to ethanol process. The resulting corn oil production is shown in Table 3. Oil production increase is compared to baseline data obtained from Polysorbate 80.

TABLE 3

| Component | Composition (wt %) | |
|---|---|---|
| Polysorbate 80 | 85% | 80% |
| Soybean Fatty Acid Methyl Ester | 5% | 5% |
| Hydrophobic Silica B | 10% | 15% |
| Oil Production Increase vs Baseline | 3% | 4% |

As shown in Table 3, the addition of hydrophobic silica resulted in additional oil production compared to baseline.

Example 4

Polysorbate 80 (Additive 1) and a blend of 85 wt % Polysorbate 80 with 10 wt % hydrophobic silica and 5 wt % soybean fatty acid methyl esters (Additive 2) were added into the syrup feed line on the inlet side of the pump feeding a disk stack centrifuge in a corn to ethanol process. The resulting corn oil production is shown in Table 4. Change in process additive dosage and change in oil production are compared to baseline data obtained from Polysorbate 80.

TABLE 4

| | Additive 1 | Additive 2 |
|---|---|---|
| Dose (ppm) | 692 | 494 |
| Change in Dose | | −29% |
| Oil Production (gal/min) | 2.3 | 2.3 |
| Change in Oil Production | | 0% |

As shown in Table 4, the addition of hydrophobic silica to the Polysorbate 80 resulted in a greater quantity of oil produced per quantity of additive used when compared to Polysorbate 80 alone.

Example 5

Polysorbate 80 and blends of Polysorbate 80 with soybean fatty acid methyl esters were added at a dosage of 626 ppm into the syrup feed line on the inlet side of the pump feeding two disk stack centrifuges in a corn to ethanol process. The resulting corn oil production is shown in Table 5.

TABLE 5

| Component | Composition (wt %) | | |
|---|---|---|---|
| Polysorbate 80 | 100% | 95% | 90% |
| Soybean Fatty Acid Methyl Ester | | 5% | 10% |
| Oil Production (gal/min) | 3.14 | 3.16 | 3.13 |

As shown in Table 5, the addition of fatty acid methyl esters to the Polysorbate 80 did not cause a significant decrease in oil production. Fatty acid methyl esters can be used to modify viscosity of the process additive system.

Example 6

The effect of hydrophobic silica content on process additive system efficacy was examined. Process additive systems were tested by addition of a 700 ppm dose to 35 mL of corn syrup at 90° C. followed by 0.5 minutes of mixing. 10 mL of each sample was transferred to a centrifuge tube and was then centrifuged for 10 minutes at 3000 rpm. The amount of oil was determined by measuring the height of the oil layer in the centrifuge tube. A control with no additive was tested for comparison.

TABLE 6

| Material | Oil Released (mm) |
|---|---|
| Control | 1.0 |
| Polysorbate 80 | 1.5 |
| Blend of Polysorbate 80 & 15 wt % Hydrophobic Silica A | 2.0 |

As can be seen in Table 6, the addition of hydrophobic silica to Polysorbate 80 resulted in significantly increased oil release when compared to Polysorbate 80 alone.

Example 7

The effect of hydrophobic silica content on process additive system efficacy was examined. Process additive systems were tested by addition of a 300 ppm dose to 80 mL of corn syrup at 90° C. then briefly mixed. 65 mL of each sample was transferred to a centrifuge tube and was then centrifuged for 2 minutes at 1700 rpm. The amount of oil was determined by measuring the height of the oil layer in the centrifuge tube.

TABLE 7

| Component | Composition (wt %) | | | | | |
|---|---|---|---|---|---|---|
| Polysorbate 80 | 100% | 99% | 95% | 90% | 85% | 80% |
| Hydrophobic Silica B | | 1% | 5% | 10% | 15% | 20% |
| Oil Released (mm) | 17 | 17 | 22 | 23 | 26 | 25 |

As can be seen in Table 7, the addition of a minimum concentration of hydrophobic silica to Polysorbate 80 resulted in significantly increased oil release when compared to Polysorbate 80 alone.

Example 8

The effect of hydrophobic silica B content on process additive system efficacy was examined. Process additive systems were tested by addition of a 300 ppm dose to 80 mL of corn syrup at 90° C. then briefly mixed. 65 mL of each sample was transferred to a centrifuge tube and was then centrifuged for 2 minutes at 1700 rpm. The amount of oil was determined by measuring the height of the oil layer in the centrifuge tube.

TABLE 8

| Component | Composition (wt %) | | | | |
|---|---|---|---|---|---|
| Polysorbate 20 | 100% | 95% | 90% | 85% | 80% |
| Hydrophobic Silica B | 0% | 5% | 10% | 15% | 20% |
| Oil Released (mm) | 9 | 26 | 32 | 35 | 32 |

As can be seen in Table 8, the addition of hydrophobic silica to Polysorbate 20 resulted in significantly increased oil release when compared to Polysorbate 20 alone.

Example 9

The effect of hydrophobic silica B content on process additive system efficacy was examined. Process additive systems were tested by addition of a 600 ppm dose to 80 mL of corn syrup at 90° C. then briefly mixed. 65 mL of each sample was transferred to a centrifuge tube and was then centrifuged for 2 minutes at 1700 rpm. The amount of oil was determined by measuring the height of the oil layer in the centrifuge tube.

TABLE 9

| Component | Composition (wt %) | | | |
|---|---|---|---|---|
| Polysorbate 20 | 100% | 95% | 90% | 85% |
| Hydrophobic Silica B | 0% | 5% | 10% | 15% |
| Oil Released (mm) | 31 | 35 | 39 | 39 |

As can be seen in Table 9, the addition of hydrophobic silica resulted in significantly increased oil release when compared to Polysorbate 20 alone.

Example 10

The effect of hydrophobic silica particle size on process additive system efficacy was examined. Process additive systems were tested by addition of a 300 ppm dose to 80 mL of corn syrup at 90° C. then briefly mixed. 65 mL of each sample was transferred to a centrifuge tube and was then centrifuged for 15 minutes at 2000 rpm. The amount of oil was determined by measuring the height of the oil layer in the centrifuge tube. Median particle size was determined using a Horiba LA-950 laser scattering particle size distribution analyzer (software version 3.29, firmware version 3.50 11/28) and fitted using a volume-based distribution. Samples were dissolved in isopropyl alcohol and analyzed using a refractive index of 1.460 for hydrophobic silica and 1.376 for isopropyl alcohol.

TABLE 10

| | Composition (wt %) | | Median | Oil |
|---|---|---|---|---|
| Sample | Polysorbate 80 | Hydrophobic Silica | Particle Size (μm) | Released (mm) |
| 1 | 100% | 0% | N/A | 33 |
| 2 | 90% | 10% | 14 | 36 |
| 3 | 90% | 10% | 0.6 | 36 |
| 4 | 90% | 10% | 21 | 35 |

As can be seen in Table 20, the addition of hydrophobic silicas of various particle sizes to Polysorbate 80 resulted in significantly increased oil release when compared to Polysorbate 80 alone.

Example 11

The effect of hydrophobic silica particle size on process additive system efficacy was examined. Process additive systems were tested by addition of a 700 ppm dose to 35 mL of corn syrup at 90° C. followed by 0.5 minutes of mixing. Next, 10 mL of treated syrup was transferred to a centrifuge tube and centrifuged for 10 minutes at 3000 rpm. The amount of oil was determined by measuring the height of the oil layer in the centrifuge tube.

TABLE 11

| Component | Composition (wt %) | | |
|---|---|---|---|
| Polysorbate 80 | 100% | 85% | 85% |
| Hydrophobic Silica A | | | 15% |
| Hydrophobic Silica B | | 15% | |
| Oil Released (mm) | 1.5 | 2.0 | 2.0 |

As can be seen in Table 11, adding either hydrophobic silica A or B to Polysorbate 80 resulted in significantly increased oil release when compared to Polysorbate 80 alone.

Example 12

The effect of hydrophobic silica with no added Polysorbate 80 (P80) on process additive system efficacy was examined. The silicas were first dispersed in corn oil to aid in process additive system addition to the corn syrup. Process additive systems were tested by addition of the specified dosage to 35 mL of corn syrup at 90° C. followed by 0.5 minutes of mixing. Next, 10 mL of treated syrup was transferred to a centrifuge tube and centrifuged for 10 minutes at 3000 rpm. The amount of oil was determined by measuring the height of the oil layer in the centrifuge tube. All silicas were dispersed in corn oil (20% by weight silica and 80% by weight corn oil) prior to addition to the syrup at the specified dosage.

TABLE 12

| | | Con- | Silica | | | | | |
|---|---|---|---|---|---|---|---|---|
| Material | P80 | trol | A | | B | | C | |
| Dose (ppm) | 700 | 0 | 525 | 2600 | 525 | 2600 | 525 | 2600 |
| Oil Released (mm) | 1.7 | 0.9 | 1.0 | 1.2 | 1.0 | 1.0 | 0.8 | 1.0 |

As can be seen in Table 12, the addition of the hydrophobic silicas alone did not produce a significant increase in oil release. P80 represents Polysorbate 80.

Example 13

The effect of the addition of fatty acid methyl ester (soybean fatty acid methyl ester) on process additive system efficacy was examined. Process additive systems were tested by addition of a 700 ppm dose to 35 mL of corn syrup at 90° C. followed by 0.5 minutes of mixing. Next, 10 mL of treated syrup was transferred to a centrifuge tube and centrifuged for 10 minutes at 3000 rpm. The amount of oil was determined by measuring the height of the oil layer in the centrifuge tube.

TABLE 13

| Component | Composition (wt %) | |
|---|---|---|
| Polysorbate 80 | 85% | 75% |
| Soybean Fatty Acid Methyl Ester | | 10% |
| Hydrophobic Silica B | 15% | 15% |
| Oil Released (mm) | 2.0 | 2.0 |

As can be seen in Table 13, the addition of fatty acid methyl ester did not have a significant adverse effect on the performance of the process additive systems containing silica.

Example 14

The effect of the type of added fatty acid methyl ester (soybean and canola methyl esters) on process additive system efficacy was examined. Process additive systems were tested by addition of a 700 ppm dose to 35 mL of corn syrup at 90° C. followed by 0.5 minutes of mixing. Next, 10 mL of treated syrup was transferred to a centrifuge tube and centrifuged for 10 minutes at 3000 rpm. The amount of oil was determined by measuring the height of the oil layer in the centrifuge tube.

TABLE 14

| Component | Composition (wt %) | | | |
|---|---|---|---|---|
| Polysorbate 80 | 87.5% | 87.5% | 72.5% | 72.5% |
| Soybean Fatty Acid Methyl Ester | 7.5% | | 12.5% | |
| Canola Fatty Acid Methyl Ester | | 7.5% | | 12.5% |
| Hydrophobic Silica A | 5.0% | 5.0% | 15.0% | 15.0% |
| Oil Released (mm) | 2.0 | 2.0 | 2.1 | 2.2 |

As can be seen in Table 14, the type of fatty acid methyl ester did not have a significant effect on the performance of the blends containing hydrophobic silica.

Example 15

The effect of the concentration of precipitated hydrophobic silica A and the presence and concentration of a fumed hydrophobic silica (hydrophobic silica C) on process additive system sedimentation was examined. Mixtures were tested by vigorously mixing a solution containing 20 g of the specified components in Table 15 then allowing them to rest, undisturbed, for 5 weeks. After this time, the sedimentation volume was measured, divided by the total volume and reported as separation. Larger values indicate more separation of the process additive system.

TABLE 15

| | Component | | | | |
|---|---|---|---|---|---|
| | Polysorbate 80 | Hydrophobic Silica A | Hydrophobic Silica B | Soybean Fatty Acid Methyl Ester | Product Stablity (Separation) |
| Composition (wt %) | 95.0% | 5.0% | | | 76.5% |
| | 94.5% | 5.0% | 0.5% | | 52.2% |
| | 94.0% | 5.0% | 1.0% | | 43.5% |
| | 93.0% | 5.0% | 2.0% | | 35.8% |
| | 89.5% | 10.0% | 0.5% | | 32.8% |
| | 89.0% | 10.0% | 1.0% | | 23.9% |
| | 88.0% | 10.0% | 2.0% | | 14.9% |
| | 85.0% | 15.0% | | | 6.0% |
| | 84.5% | 15.0% | 0.5% | | 3.0% |
| | 84.0% | 15.0% | 1.0% | | 1.5% |
| | 83.0% | 15.0% | 2.0% | | 0.0% |
| | 80.0% | 20.0% | | | 0.0% |
| | 75.0% | 20.0% | | 5.0% | 0.0% |
| | 79.0% | 20.0% | 1.0% | | 0.0% |
| | 74.0% | 20.0% | 1.0% | 5.0% | 0.0% |

As can be seen in Table 15, increasing the concentration of the precipitated hydrophobic silica increased the sedimentation stability of the process additive system. The addition of hydrophobic fumed silica increased the stability of the process additive system with higher concentrations yielding more stable process additive systems.

Example 16

The effect of the concentration of hydrophobic silica on the viscosity of the process additive system was examined. Viscosity was tested using a Brookfield DV-II Pro Viscometer with #6 RV spindle at room temperature (~24° C.) at 50 RPM.

TABLE 16

| Component | Composition (wt %) | | | |
|---|---|---|---|---|
| Polysorbate 80 | 100% | 95% | 90% | 85% |
| Hydrophobic Silica B | | 5% | 10% | 15% |
| Viscosity (cP) | 540 | 1080 | 2520 | 6780 |

As can be seen in Table 16, varying the concentration of hydrophobic silica can be used to modify the viscosity of the process additive system.

Example 17

The effect of hydrophobic silica particle size on the viscosity of the process additive system was examined. Viscosity was tested using a Brookfield DV-II Pro Viscometer with #6 RV spindle at room temperature (~24° C.) at 50 RPM.

TABLE 17

| Component | Composition (wt %) | |
|---|---|---|
| Polysorbate 80 | 85% | 85% |
| Hydrophobic Silica A | 15% | |
| Hydrophobic Silica B | | 15% |
| Viscosity (cP) | 3900 | 6780 |

As can be seen in Table 17, hydrophobic silicas with different particle sizes can be used to modify the viscosity of the process additive system.

Example 18

The effect of the addition of fumed hydrophobic silica particle size on the viscosity of the process additive system was examined. Viscosity was tested using a Brookfield DV-II Pro Viscometer with #6 RV spindle at room temperature (~24° C.) at 50 RPM.

TABLE 18

| Component | Composition (wt %) | | | |
|---|---|---|---|---|
| Polysorbate 80 | 85% | 84.5% | 84% | 83% |
| Hydrophobic Silica A | 15% | 15% | 15% | 15% |
| Hydrophobic Silica C | | 0.5% | 1% | 2% |
| Viscosity (cP) | 3900 | 4180 | 5960 | 10640 |

As can be seen in Table 18, the addition of fumed hydrophobic silicas can be used to modify the viscosity of the process additive system.

Example 19

The effect of fatty acid methyl ester addition on the viscosity of the process additive system was examined. Viscosity was tested using a Brookfield DV-II Pro Viscometer with #6 RV spindle at room temperature (~24° C.) at 50 RPM.

TABLE 19

| Component | Composition (wt%) | | | |
| --- | --- | --- | --- | --- |
| Polysorbate 80 | 85% | 80% | 75% | 70% |
| Soybean Fatty Acid Methyl Ester | | 5% | 10% | 15% |
| Hydrophobic Silica B | 15% | 15% | 15% | 15% |
| Viscosity (cP) | 6780 | 4800 | 3820 | 3040 |

As can be seen in Table 19, the addition of fatty acid methyl esters can be used to modify the viscosity of the process additive system.

Example 20

The effect of hydrophilic silica on the viscosity of the process additive system was examined. A mixture containing about 13% by weight of hydrophilic silica with particle size of 9 μm, about 1% by weight soybean fatty acid methyl ester, and 86% by weight Polysorbate 80 formed a gel and did not flow upon inversion of the sample. This demonstrates the ability of hydrophilic silica to modify the viscosity of the process additive system.

The invention claimed is:

1. A method for recovering oil from grain to ethanol production, the method comprising the step of adding a process additive system to a process stream wherein the process additive system comprises at least one chemical additive and at least one hydrophobic silica with particle size of at least 0.01 μm,
wherein the total silica content of the process additive system is in an amount of from 3% to 50% by weight based on the weight of the process additive system, and
wherein the chemical additive comprises at least one functionalized polyol derived from a sorbitol, a sorbitan, isosorbide, sucrose, or glycerol.

2. The method of claim 1 wherein the functionalized polyol comprises at least one alkoxylated sorbitan alkylate.

3. The method of claim 2 wherein the chain length of the alkylate is from 6 to 24 carbons.

4. The method of claim 2 wherein the alkoxylated sorbitan alkylate has been alkoxylated with from 5 to 60 moles of alkyl oxide.

5. The method of claim 4 wherein the alkyl oxide is selected from ethylene oxide, propylene oxide and mixtures thereof.

6. The method of claim 2 wherein the alkoxylated sorbitan alkylate is selected from the group consisting of an alkoxylated sorbitan monolaurate, alkoxylated sorbitan monooleate, alkoxylated sorbitan monopalmitate alkoxylated sorbitan monostearate and combination thereof.

7. The method of claim 2 wherein the alkoxylated sorbitan alkylate comprises an alkoxylated sorbitan monolaurate.

8. The method of claim 2 wherein the alkoxylated sorbitan alkylate comprises an alkoxylated sorbitan monooleate.

9. The method of claim 1 wherein the median particle size of silica is from about 0.01 to about 200 μm.

10. The method of claim 1 further comprising one or more modifiers to adjust the sedimentation stability, rheological properties, and/or elastic properties of the process additive system.

11. The method of claim 1 wherein the total silica content is from about 3% to about 30% by weight based on the weight of the process additive system.

12. The method of claim 1 wherein the total silica content is from greater than 5% to about 50% by weight based on the weight of the process additive system.

13. The method of claim 10 wherein the modifiers are selected from the groups consisting of fatty acid alkyl esters, monoglycerides, diglycerides, triglycerides, mineral oils, alcohols and combinations thereof.

14. The method of claim 12 wherein the modifiers comprise fatty acid alkyl esters and/or triglycerides.

15. The method of claim 10 wherein the modifiers are from about 0.1% to about 30% by weight based on the weight of the process additive system.

16. The method of claim 1 wherein the amount of process additive system added is from about 20 ppm to about 10,000 ppm based on weight of the process stream.

17. The method of claim 1 wherein the process additive system is heated from about 18° C. to 100° C. prior to the addition to the process stream.

18. The method of claim 1 wherein at least one addition point of the process additive system in the process stream is selected from the whole stillage process stream prior to separation into wet cake and thin stillage, the process stream at or near the inlet to the centrifuge or after the solid separation centrifuge, prior to or at the inlet and/or outlet of one or more of the thin stillage evaporators, in the evaporators, to the syrup just prior to the oil separation centrifuge, at the inlet of the premix or retention heat tanks, a point after the syrup feed tank and before the centrifuge and any combination thereof.

19. The method of claim 1 wherein the process additive system is added at more than one addition point to the process stream.

20. The method of claim 1 wherein the grain is corn.

* * * * *